(12) United States Patent
Filippini et al.

(10) Patent No.: US 7,709,030 B2
(45) Date of Patent: May 4, 2010

(54) COMPOSITIONS OF CUPRIC SALTS AND THEIR USE FOR THE CONTROL OF PHYTOPATHOGENTIC FUNGI

(75) Inventors: Lucio Filippini, Milanese-Milan (IT); Mauro Vanzulli, Saronno-Varese (IT); Filippo Faccini, Gallo-Ferrara (IT)

(73) Assignee: Isagro S.p.A., Milan (IT)

( * ) Notice: Subject to any disclaimer, the term of this patent is extended or adjusted under 35 U.S.C. 154(b) by 626 days.

(21) Appl. No.: 10/503,107

(22) PCT Filed: Jan. 30, 2003

(86) PCT No.: PCT/EP03/00950

§ 371 (c)(1), (2), (4) Date: Jan. 24, 2005

(87) PCT Pub. No.: WO03/065810

PCT Pub. Date: Aug. 14, 2003

(65) Prior Publication Data

US 2005/0123622 A1 Jun. 9, 2005

(30) Foreign Application Priority Data

Feb. 5, 2002 (IT) .......................... MI2002A0205

(51) Int. Cl.
*A01N 59/20* (2006.01)
(52) U.S. Cl. ...................... 424/632; 424/633
(58) Field of Classification Search ................ 424/633, 424/635, 638, 632
See application file for complete search history.

(56) References Cited

U.S. PATENT DOCUMENTS

| | | | | |
|---|---|---|---|---|
| 4,075,326 A | | 2/1978 | Kuyama | |
| 4,503,042 A | * | 3/1985 | Caprioli et al. | ............. 424/632 |

FOREIGN PATENT DOCUMENTS

| | | | |
|---|---|---|---|
| CH | 452990 | * | 3/1968 |
| ES | 2 115 491 | | 6/1998 |
| ES | 2 116 191 | | 7/1998 |
| GB | 728520 | | 4/1955 |
| GB | 940764 | | 11/1963 |
| GB | 2 016 924 | | 9/1979 |
| WO | WO 91/13552 | | 9/1991 |
| WO | WO02/833566 | | 10/2002 |

OTHER PUBLICATIONS

Derwent abstract 1967-03026H, abstracting CH 452990 (1968).*
Partial Translation of CH 452,990 (1968).*
Lewis, Richard J., Sr., Hawley's Condense Chemical Dictionary, 13$^{th}$ ed., John Wiley & Sons, Inc., 1997, p. 301.*
Kirk-Othmer Encyclopedia of Chemical Technology, 4$^{th}$ ed., John Wiley & Sons, New York, vol. 7, pp. 505-518 (1993).*
Ullmann's Encyclopedia of Industrial Chemistry, 5$^{th}$ ed., VCH Verlagsgesellschaft mbH, Weinheim, Germany, vol. A7, pp. 567-583 (1986).*

* cited by examiner

*Primary Examiner*—John Pak
(74) *Attorney, Agent, or Firm*—Hedman & Costigan, P.C.; James V. Costigan

(57) ABSTRACT

A description follows of mixtures of copper (II) hydroxide with at least one other cupric salt having the formula (A) and their use for the control of phytopathogenic fungi.

5 Claims, No Drawings

COMPOSITIONS OF CUPRIC SALTS AND THEIR USE FOR THE CONTROL OF PHYTOPATHOGENTIC FUNGI

The present invention relates to compositions based on cupric salts and their use for the control of phytopathogenic fungi.

In particular, the present invention relates to compositions based on cupric salts capable of effectively controlling phytopathogens which cause damage to crops of economic interest.

Cupric hydroxide, cupric oxychloride ($3Cu(OH)_2 \cdot CuCl_2$), calcium cupric oxychloride ($3Cu(OH)_2 \cdot CaCl_2$), tribasic cupric sulfate ($3Cu(OH)_2 \cdot CuSO_4$), Bordeaux mixture ($3Cu(OH)_2 \cdot CaSO_4$), are active principles which are well known for being used singly in applications on the leaves for the control of phytopathogens. These cupric active principles are described, for example in "THE PESTICIDE MANUAL, 12th EDITION, BRITISH CROP PROTECTION COUNCIL, Pages 200-205".

It is known and recognized that cupric hydroxide is more effective with respect to other cupric species, which allows it to be used at lower doses. At the same time, however, cupric hydroxide has a greater phytotoxicity.

The applicant has now found that mixtures of copper (II) hydroxide allows the drawbacks of the known art to be overcome.

An object of the present invention therefore relates to mixtures of copper(II) hydroxide with at least one other cupric salt having formula (A):

$$3Cu(OH)_2 \cdot X(Y)_n \quad (A)$$

wherein:

X represents the copper(II) or calcium (II) ion;

Y has the meaning of a chloride or sulfate ion;

n is an integer which can have the value of 1 or 2.

A further object of the present invention relates to the use of mixtures of copper(II) hydroxide with at least one other cupric salt having formula (A)

$$3Cu(OH)_2 \cdot X(Y)_n \quad (A)$$

wherein:

X represents the copper(II) or calcium (II) ion;

Y has the meaning of a chloride or sulfate ion;

n is an integer which can have the value of 1 or 2.

for the control of phytopathogenic fungi in agricultural crops.

An object of the present invention preferably relates to mixtures of copper(II) hydroxide with cupric oxychloride ($3Cu(OH)_2 \cdot CuCl_2$), or calcium cupric oxychloride ($3Cu(OH)_2 \cdot CaCl_2$), or tribasic cupric sulfate ($3Cu(OH)_2 \cdot CuSO_4$), or Bordeaux mixture ($3Cu(OH)_2 \cdot CaSO_4$), and their use for the control of phytopathogens.

Mixtures of copper(II) hydroxide with at least one other cupric salt, such as cupric oxychloride ($3Cu(OH)_2 \cdot CuCl_2$), calcium cupric oxychloride ($3Cu(OH)_2 \cdot CaCl_2$), tribasic cupric sulfate ($3Cu(OH)_2 \cdot CuSO_4$), Bordeaux mixture ($3Cu(OH)_2 \cdot CaSO_4$), do, in fact, have an unexpected synergistic action which allows the control of many phytopathogenic agents, at the same time enabling lower doses of metallic copper to be used, with respect to those normally adopted for the single components.

The compositions, object of the present invention, are consequently capable of effectively controlling numerous phytopathogens which cause considerable damage to crops of economic interest.

Examples of phytopathogenic fungi which can be effectively controlled with the compositions of the invention are *Plasmopara viticola*, *Phytophthora infestans*, *Bremia lactucae*, *Venturia inaequalis*.

The mixtures, object of the present invention, can be obtained by mechanically mixing suitable quantities of copper(II) hydroxide and one or more cupric salts having formula A as defined above, or by mixing single salts already formulated in the form of specific compositions.

Alternatively, the mixtures, object of the present invention, can also be prepared by the partial transformation of a suspension of cupric salts having formula A selected from cupric chloride, cupric sulfate or cupric oxychloride, with an alkaline hydroxide, such as sodium or potassium or calcium hydroxide. The conditions of these reactions can be extracted, for example, from International Publication No. WO 02/083566, suitably reducing the prescribed quantities of alkaline hydroxide.

The weight ratio between copper(II) hydroxide and the cupric salt having formula (A) in the above mixtures, can vary from 1:20 to 20:1, preferably from 1:10 to 10:1, in particular from 1:2 to 2:1.

These mixtures can be used in agronomic practice for applications on plants or a part thereof, in particular on all parts of the plant, on the leaves, stems, branches and roots, or on the earth in which the plant grows.

The mixtures, object of the present invention, can be conveniently used in agronomic practice alone or combined with other active principles (fungicides).

An object of the present invention therefore also relates to the use of said mixtures in a combination with one or more other active principles both as specifically prepared compositions or as an extemporaneous blending of the single components.

As an illustrative but non-limiting example, some active principles which can be conveniently used in a mixture with the compounds, object of the present invention, are listed below:

cymoxanil, fosetyl, benalaxyl, benalaxyl-M (R isomer of benalaxyl), metalaxyl, oxadixyl, ofurace, mancozeb, maneb, zineb, fenamidone, famoxadone, procymidone, chlozolinate, vinclozolina, iprovalicarb, dimethomorph, propamocarb, prothiocarb, hymenaxol, pencicuron, etridiazole, analogous synthetic products of strobilurines (such as azoxystrobin, kresoxim methyl), captane, folpet, dinocap, sulfur, thiram, tolclofos methyl, chlorothalonil, azoles inhibitors of the biosynthesis of ergosterol (such as tetraconazole myclobutanyl, hexaconazole, epoxy-conazole), micro-organisms (such as Ampelomyces quisqualis), BAS512, IKF916, IR5885, ethaboxam, zoxamide, fluazinam.

In order to be conveniently used in agriculture, the mixtures, object of the present invention, and also combinations of said mixtures with one or more other active principles, can also be suitably formulated in order to favour the distribution and adhesion to the vegetable to be protected.

Compositions in the form of wettable powders, concentrated suspensions, granulates, etc., can be used.

The compositions are prepared with known methods, for example by diluting the active substances with liquid or solid mediums, optionally in the presence of surface-active agents.

Liquid diluents which can be used are, for example: water, aromatic or paraffinic organic solvents, alcohols, esters, ketones, amides.

Solid diluents, or also carriers, which can be used are, for example: silica, kaolin, bentonite, talc, infusorial earth, dolomite, calcium carbonate, magnesia, chalk, clays, synthetic silicates, attapulgite, seppiolite.

Surface-active agents which can be used are, for example: salts of sodium, potassium, triethanolamine of: alkyl naphthalene sulfonates, condensed alkyl naphthalene sulfonates, phenyl sulfonates, polycarboxylates, sulfosuccinates, alkyl sulfo-succinates, alkyl sulfates, lignin sulfonates, polyethoxylated fatty alcohols, alkylaryl sulfonates, polyethoxylated alkyl phenols, polyethoxylated esters of sorbitol, polypropoxy polyethoxylates (block polymers).

The compositions can also contain special additives for particular purposes, such as, for example antifreeze agents: propylene glycol, or adhesion agents such as Arabic rubber, polyvinyl alcohol, polyvinyl pyrrolidone, etc.

In the formulations, the percentage content of the mixtures, object of the present invention, can vary from 1% to 95%, preferably from 5% to 70%.

The following examples are exclusively provided for illustrative purposes and do not limit the scope of the present invention.

EXAMPLE 1

Preparation of a Wettable Powder.

A formulation of the wettable powder type at 50% of copper (WP 50) was prepared by suitably mixing and grinding the following ingredients:

| INGREDIENTS | QUANTITY % (w/w) |
|---|---|
| Technical cupric hydroxide at 93.7% | 41.0 |
| (Cu content = 61%) | (equal to 25% of Cu) |
| Technical cupric oxychloride at 96.6% | 43.5 |
| (Cu content = 57.5%) | (equal to 25% of Cu) |
| Alkyl sodium naphthalenesulfonate | 1.5 |
| Sodium polycarboxylate | 1.0 |
| Sodium lignin sulfonate | 3.0 |
| Silica | 1.0 |
| Calcium carbonate | 9.0 |

EXAMPLE 2

Preparation of a Concentrated Suspension

A formulation of the concentrated suspension type at 20% of copper (SC20) was prepared by suitably mixing and grinding the following ingredients:

| INGREDIENTS | QUANTITY % (w/w) |
|---|---|
| Technical cupric hydroxide at 93.7% | 16.4 |
| (Cu content = 61%) | (equal to 10% of Cu) |
| Technical cupric oxychloride at 96.6% | 17.4 |
| (Cu content = 57.5%) | (equal to 10% of Cu) |
| Polyethoxylated fatty alcohol | 2.5 |
| Polyethoxylated alkylaryl phenol, Triethanol amine salt | 2.5 |
| Polysaccharide | 0.3 |
| Propylene glycol | 4.0 |
| Preservative | 0.4 |
| Anti-foam agent | 0.1 |
| Water | 56.7 |

EXAMPLE 3

Preparation of Dispersible Granules

A formulation of the dispersible granule type at 50% of copper (WG 50) in water, was prepared by suitably mixing, grinding and granulating the following ingredients:

| INGREDIENTS | QUANTITY % (w/w) |
|---|---|
| Technical cupric hydroxide at 93.7% | 41.0 |
| (Cu content = 61%) | (equal to 25% of Cu) |
| Technical cupric oxychloride at 96.6% | 43.5 |
| (Cu content = 57.5%) | (equal to 25% of Cu) |
| Alkyl sodium naphthalene sulfonate | 1.0 |
| Sodium polycarboxylate | 2.0 |
| Sodium lignin sulfonate | 8.0 |
| Kaolin | 4.5 |

EXAMPLE 4

Determination of the Biological Efficacy in Greenhouse.

Using the composition described in Example 1, a greenhouse test was carried out, for the control of *Phytophthora infestans* (tomato mildew) compared with commercial formulation of cupric hydroxide and cupric oxychloride used singly. A random block experimental scheme was used, which included 3 replications and 10 plants for each lot. An artificial inoculation of the pathogen was effected 24 h after the treatment with the product.

The degree of action of the products was recorded after 7 days.

The synergistic effect of the mixture was evaluated by comparing the experimental data obtained with the theoretical efficacy value calculated according to the Limpel formula ("Pesticide Science" (1987), vol. 19, pages 309-315:

$$E = x + y - xy/100$$

wherein:
E is the expected fungicidal activity from a mixture obtained by mixing g·x of the compound X with g·y of the compound Y;
x is the activity of the compound X when used alone at a dose of g·x;
y is the activity of the compound Y when used alone at a dose of g·y.

An experimental fungicidal activity higher than the calculated value of E, should be considered as being a synergistic effect.

The data obtained are indicated in Table 1.

TABLE 1

| Formulation | Application dose of formulate (g/hl) | Corresponding cupric dose (g/hl) | Expected efficacy (Limpel) | Observed efficacy | Observed efficacy/ expected efficacy |
|---|---|---|---|---|---|
| Cupric hydroxide (WP 40%) | 100 | 40 | — | 38 | |

TABLE 1-continued

| Formulation | Application dose of formulate (g/hl) | Corresponding cupric dose (g/hl) | Expected efficacy (Limpel) | Observed efficacy | Observed efficacy/ expected efficacy |
|---|---|---|---|---|---|
| Cupric oxychloride (WP 50%) | 80 | 40 | — | 31 | |
| Cupric hydroxide + Cupric oxychloride (50% WP) | 160 | 80 | 57.2 | 80 | 1.40 |

EXAMPLE 5

Determination of the Biological Efficacy in the Field.

A field efficacy test was carried out, using the composition described in Example 1, for the control of *Plasmopara viticola* (vine mildew) compared with commercial formulations of cupric hydroxide and cupric oxychloride used singly. A random block experimental scheme was used which included 4 replications and 15 plants for each parcel. Calendar treatments were effected (7-8 days) and the degree of action of the products was registered 12 days after the fifth and last treatment, compared with the non-treated blank; the synergistic effect of the mixture was evaluated on the basis of the expected efficacy according to Limpel.

The data obtained are indicated in Table 2.

TABLE 2

| Formulation | Application dose of formulate (g/hl) | Corresponding cupric dose (g/hl) | Expected efficacy (Limpel) | Observed Efficacy | Efficacy observed/ efficacy expected |
|---|---|---|---|---|---|
| Cupric hydroxide (WP 40%) | 100 | 40 | — | 35 | |
| Cupric oxychloride (WP 50%) | 80 | 40 | — | 30 | |
| Cupric hydroxide + Cupric oxychloride (50% WP) | 160 | 80 | 54.5 | 75 | 1.37 |

What we claim is:

1. A mixture consisting of copper (II) hydroxide with one other cupric salt having formula (A):

$$3Cu(OH)_2 \cdot X(Y)_n \quad (A)$$

wherein:
   X represents the copper (II) ion;
   Y has the meaning of a chloride ion;
   n is an integer which has the value of 2; and
   the weight ratio between copper (II) hydroxide and the cupric salt having formula (A) ranges from 1:2 to 2:1.

2. A method for controlling phytopathogenic fungi in agricultural crops which comprises applying the mixture according to claim 1 to said phytopathogenic fungi on agricultural crops.

3. The method according to claim 2, characterized in that the mixture is applied to all parts of the plant, on the leaves, stems, branches and roots, or on the earth in which the plant grows.

4. A method for the control of phytopathogenic fungi which comprises applying to pathogenic fungi a mixture of copper (II) hydroxide with one other cupric salt having formula (A):

$$3Cu(OH)_2 \cdot X(Y)_n \quad (A)$$

wherein:
   X represents the copper (II) ion;
   Y has the meaning of a chloride ion;
   n is an integer which has the value of 2; and
   the weight ratio between copper (II) hydroxide and the cupric salt having formula (A) ranges from 1:2 to 2:1.

5. The method according to claim 4, wherein the phytopathogenic fungi are *Plasmopara viticola, Phytophthora infestans, Bremia lactucae, Venturia inaequalis*.

* * * * *